United States Patent
Lakkapragada et al.

(10) Patent No.: US 7,767,956 B2
(45) Date of Patent: *Aug. 3, 2010

(54) METHODS AND SYSTEMS FOR LITHOGRAPHY PROCESS CONTROL

(75) Inventors: Suresh Lakkapragada, Santa Clara, CA (US); Kyle A. Brown, San Diego, CA (US); Matt Hankinson, San Jose, CA (US); Ady Levy, Sunnyvale, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/328,123

(22) Filed: Dec. 4, 2008

(65) Prior Publication Data

US 2009/0079974 A1    Mar. 26, 2009

Related U.S. Application Data

(63) Continuation of application No. 11/345,145, filed on Feb. 1, 2006, now Pat. No. 7,462,814, which is a continuation of application No. 10/401,509, filed on Mar. 27, 2003, now abandoned, which is a continuation of application No. 09/849,622, filed on May 4, 2001, now Pat. No. 6,689,519.

(60) Provisional application No. 60/202,372, filed on May 4, 2000.

(51) Int. Cl.
  *G06M 7/00* (2006.01)
  *H01J 40/14* (2006.01)

(52) U.S. Cl. .......... 250/221; 250/559.3; 250/559.33; 250/559.4; 250/548; 250/559.44; 356/400; 356/401; 356/237.2; 356/237.5; 356/947; 382/144; 382/145; 382/151; 382/153; 414/935

(58) Field of Classification Search .......... 250/559.3, 250/559.33, 559.4, 559.44, 559.04, 548, 250/221; 356/400–401, 237.2–237.5, 947, 356/445, 446; 382/144, 145, 149, 151, 153; 414/935, 940, 936

See application file for complete search history.

(56) References Cited

U.S. PATENT DOCUMENTS 4,631,416 A    12/1986    Trutna, Jr.

(Continued)

FOREIGN PATENT DOCUMENTS

EP    1065567    1/2001

(Continued)

OTHER PUBLICATIONS

International Search Report, application No. PCT/US01/14367, mailed Aug. 15, 2001.

(Continued)

*Primary Examiner*—Georgia Y Epps
*Assistant Examiner*—Francis M Legasse, Jr.
(74) *Attorney, Agent, or Firm*—Ann Marie Mewherter

(57) ABSTRACT

Methods and systems for evaluating and controlling a lithography process are provided. For example, a method for reducing within wafer variation of a critical metric of a lithography process may include measuring at least one property of a resist disposed upon a wafer during the lithography process. A critical metric of a lithography process may include, but may not be limited to, a critical dimension of a feature formed during the lithography process. The method may also include altering at least one parameter of a process module configured to perform a step of the lithography process to reduce within wafer variation of the critical metric. The parameter of the process module may be altered in response to at least the one measured property of the resist.

19 Claims, 5 Drawing Sheets

U.S. PATENT DOCUMENTS

| | | |
|---|---|---|
| 4,999,014 A | 3/1991 | Gold et al. |
| 5,042,951 A | 8/1991 | Gold et al. |
| 5,114,235 A | 5/1992 | Suda et al. |
| 5,182,455 A | 1/1993 | Muraki |
| 5,182,610 A | 1/1993 | Shibata |
| 5,189,494 A | 2/1993 | Muraki |
| 5,216,257 A | 6/1993 | Brueck et al. |
| 5,316,984 A | 5/1994 | Leourx |
| 5,327,221 A | 7/1994 | Saitoh et al. |
| 5,340,992 A | 8/1994 | Matsugu et al. |
| 5,412,473 A | 5/1995 | Rosencwaig et al. |
| 5,414,514 A | 5/1995 | Smith et al. |
| 5,516,608 A | 5/1996 | Hobbs et al. |
| 5,581,350 A | 12/1996 | Chen et al. |
| 5,596,406 A | 1/1997 | Rosencwaig et al. |
| 5,596,411 A | 1/1997 | Fanton et al. |
| 5,608,526 A | 3/1997 | Piwonka-Corle et al. |
| 5,619,548 A | 4/1997 | Koppel |
| 5,666,196 A | 9/1997 | Ishii et al. |
| 5,689,614 A | 11/1997 | Gronet et al. |
| 5,703,692 A | 12/1997 | McNeil |
| 5,747,813 A | 5/1998 | Norton et al. |
| 5,771,094 A | 6/1998 | Carter et al. |
| 5,773,174 A | 6/1998 | Koizumi et al. |
| 5,783,342 A | 7/1998 | Yamashita et al. |
| 5,798,837 A | 8/1998 | Aspnes et al. |
| 5,801,390 A | 9/1998 | Shiraishi |
| 5,808,742 A | 9/1998 | Everett et al. |
| 5,859,424 A | 1/1999 | Norton et al. |
| 5,877,859 A | 3/1999 | Aspnes et al. |
| 5,877,861 A | 3/1999 | Ausschnitt et al. |
| 5,889,593 A * | 3/1999 | Bareket ...................... 356/445 |
| 5,900,939 A | 5/1999 | Aspnes et al. |
| 5,910,842 A | 6/1999 | Piwonka-Corle et al. |
| 5,917,588 A | 6/1999 | Addiego |
| 5,917,594 A | 6/1999 | Norton |
| 5,965,306 A | 10/1999 | Mansfield et al. |
| 5,968,691 A | 10/1999 | Yoshioka et al. |
| 5,973,787 A | 10/1999 | Aspens et al. |
| 5,991,699 A | 11/1999 | Kulkarni et al. |
| 5,994,036 A | 11/1999 | Itoh |
| 6,023,338 A | 2/2000 | Bareket |
| 6,046,094 A | 4/2000 | Jost et al. |
| 6,077,756 A | 6/2000 | Lin et al. |
| 6,079,256 A | 6/2000 | Bareket |
| 6,128,089 A | 10/2000 | Ausschnitt et al. |
| 6,153,886 A | 11/2000 | Hagiwara et al. |
| 6,157,452 A | 12/2000 | Hasegawa et al. |
| 6,177,330 B1 | 1/2001 | Yasuda |
| 6,255,189 B1 | 7/2001 | Muller et al. |
| 6,259,521 B1 | 7/2001 | Miller et al. |
| 6,301,001 B1 | 10/2001 | Unno |
| 6,301,011 B1 | 10/2001 | Fung et al. |
| 6,317,211 B1 | 11/2001 | Ausschnitt et al. |
| 6,388,253 B1 | 5/2002 | Su |
| 6,417,922 B1 | 7/2002 | Dirksen et al. |
| 6,421,124 B1 | 7/2002 | Matsumoto et al. |
| 6,462,818 B1 | 10/2002 | Bareket |
| 6,476,920 B1 | 11/2002 | Scheiner et al. |
| 6,484,060 B1 | 11/2002 | Baluswamy et al. |
| 6,486,492 B1 | 11/2002 | Su |
| 6,486,954 B1 | 11/2002 | Mieher et al. |
| 6,515,745 B2 | 2/2003 | Vurens et al. |
| 6,649,923 B2 | 11/2003 | Matsumoto |
| 6,690,473 B1 | 2/2004 | Stanke et al. |
| 6,699,624 B2 | 3/2004 | Nui et al. |
| 6,730,925 B1 * | 5/2004 | Ozawa ...................... 250/548 |
| 6,972,852 B2 | 12/2005 | Opsal et al. |
| 6,987,572 B2 | 1/2006 | Lakkapragada et al. |
| 2002/0018217 A1 | 2/2002 | Weber-Grabau et al. |
| 2002/0149782 A1 | 10/2002 | Raymond |
| 2002/0158193 A1 | 10/2002 | Sezginer et al. |
| 2002/0192577 A1 | 12/2002 | Fay et al. |

FOREIGN PATENT DOCUMENTS

| | | |
|---|---|---|
| EP | 1066925 | 1/2001 |
| WO | WO 99/02970 | 1/1999 |
| WO | WO 99/25004 | 5/1999 |
| WO | WO 99/41434 | 8/1999 |
| WO | WO 99/45340 | 9/1999 |
| WO | WO 01/09566 | 2/2001 |
| WO | WO 02/15238 | 2/2002 |
| WO | WO 02/25723 | 3/2002 |
| WO | WO 02/069390 | 9/2002 |

OTHER PUBLICATIONS

Korth, "Phase-Sensitive Overlay Analysis Spectrometry," IBM Technical Disclosure Bulletin, Mar. 1990, pp. 170-174 (printed from the Internet on 3 pages).

McNeil et al., "Scatterometry Applied to Microelectronics Processing," Microlithography World, Nov./Dec. 1992, pp. 16-22.

Raymond et al, "Metrology of subwavelength photoresist gratings using optical scatterometry," J. Vac. Sci. Technol. B 13(4), Jul./Aug. 1995, pp. 1484-1495.

Raymond et al., "Scatterometry for CD measurements of etched structures," SPIE vol. 2725, 1996, pp. 720-728.

Sturtevant et al., "Use of scatterometric latent image detector in closed loop feedback control of linewidth," SPIE vol. 2196, 1994, pp. 352-359.

Wittekoek et al., "In-process Image Detecting Technique for Determination of Overlay, and Image Quality for ASM-L Wafer Stepper," SPIE vol. 1674, 1992, pp. 594-608.

* cited by examiner

METHODS AND SYSTEMS FOR LITHOGRAPHY PROCESS CONTROL

PRIORITY CLAIM

This application is a continuation of Ser. No. 11/345,145 filed on Feb. 1, 2006, now U.S. Pat. No. 7,462,814, which is a continuation of Ser. No. 10/401,509 filed Mar. 27, 2003, now abandoned, which is a continuation of Ser. No. 09/849,622 filed May 4, 2001, now U.S. Pat. No. 6,689,519, which claims the benefit of Ser. No. 60/202,372 filed May 4, 2000.

BACKGROUND OF THE INVENTION

1. Field of the Invention

This invention generally relates to systems and methods for evaluating and controlling semiconductor fabrication processes. Certain embodiments relate to systems and methods for evaluating and/or controlling a lithography process by measuring a property of a resist and controlling a process step involved in the lithography process.

2. Description of the Related Art

Semiconductor fabrication processes typically involve a number of lithography steps to form various features and multiple levels of a semiconductor device. Lithography involves transferring a pattern to a resist formed on a semiconductor substrate, which may be commonly referred to as a wafer. A reticle, or a mask, may be disposed above the resist and may have substantially transparent regions and substantially opaque regions configured in a pattern that may transferred to the resist. As such, substantially opaque regions of the reticle may protect underlying regions of the resist from exposure to an energy source. The resist may, therefore, be patterned by selectively exposing regions of the resist to an energy source such as ultraviolet light, a beam of electrons, or an x-ray source. The patterned resist may then be used to mask underlying layers in subsequent semiconductor fabrication processes such as ion implantation and etch. Therefore, a resist may substantially inhibit an underlying layer such as a dielectric material or the semiconductor substrate from implantation of ions or removal by etch.

As the features sizes of semiconductor devices continue to shrink, the minimum feature size which may be successfully fabricated may often be limited by performance characteristics of a lithography process. Examples of performance characteristics of a lithography process include, but are not limited to, resolution capability, across chip linewidth variations, and across wafer linewidth variations. In optical lithography, performance characteristics such as resolution capability of the lithography process may often be limited by the quality of the resist application, the performance of the resist, the exposure tool, and the wavelength of light which is used to expose the resist. The ability to resolve a minimum feature size, however, may also be strongly dependent on other critical parameters of the lithography process such as a temperature of a post exposure bake process or an exposure dose of an exposure process. As such, controlling the critical parameters of lithography processes is becoming increasingly important to the successful fabrication of semiconductor devices.

One strategy to improve the performance characteristics of a lithography process may involve controlling and reducing variations in critical parameters of the lithography process. For example, one critical parameter in a lithography process may be the post exposure bake temperature. In particular, a chemical reaction in an exposed portion of a chemically amplified resist may be driven and controlled by heating the resist subsequent to the exposure process. Such a resist may include, but may not be limited to, a resin and a photo-acid generating compound. The temperature of a post exposure bake process may drive generation and diffusion of a photo-generated acid in the resist that causes deblocking of the resin. Deblocking of the resin may substantially alter the solubility of the resist such that it may be removed by exposure to an aqueous developer solution in a subsequent developing process. As such, temperature-controlled diffusion in the exposed resist may affect physical dimensions of remaining resist, or resolved features. Furthermore, variations in temperature across a bake plate of a post exposure bake process module may cause variations in the dimensions of the features at various positions on a wafer. Therefore, the resolution capability of a lithography process may be improved by reducing temperature variations across the bake plate of a post exposure bake process module.

There are several disadvantages, however, in using currently available methods to improve the resolution capability of lithography processes. For example, currently available methods may not account for degradation in the uniformity of a critical parameter over time. For a post exposure bake module, thermal relaxation of heating elements, contamination, or other performance variations may adversely affect the resolution capability of a lithography process to various degrees over time. As such, monitoring and controlling time-dependent variations in the critical parameters may maintain and improve the performance characteristics of a lithography process. In addition, integrated control mechanisms that may currently be used to monitor variations in the temperature of the post exposure bake module may control and alter the process at the wafer level. Therefore, all positions, or fields, on the wafer are affected equally and improvements are made for an average performance across the wafer. In this manner, systematic variations in the resolution capability from field to field across a wafer may not be monitored or altered, which may have an adverse affect on the overall performance characteristics of a lithography process.

Accordingly, it may be advantageous to develop a method and a system to evaluate and control a lithography process such that within wafer variability of critical dimensions of features formed by a lithography process may be reduced.

SUMMARY OF THE INVENTION

An embodiment of the invention relates to a method for reducing within wafer ("WIW") variation of a critical metric of a lithography process. A critical metric of a lithography process may include, but is not limited to, a critical dimension of features formed during the lithography process and overlay. Critical dimensions of features formed during a lithography process may include, for example, a width, a height, and a sidewall profile of the features. Overlay generally refers to a lateral position of a feature on one level of a wafer with respect to a lateral position of a feature on another level of the wafer. The lithography process may include optical lithography, e-beam lithography, or x-ray lithography.

The method may include measuring at least one property of a resist disposed upon a wafer during the lithography process. For example, the method may include measuring at least the one property of the resist at various locations across the wafer. In addition, the method may include measuring at least the one property of the resist between steps of the lithography process or during a step of the lithography process. Furthermore, the method may include measuring at least one property of a resist disposed upon at least two wafers during the lithography process. At least the one property may include, but may not be limited to, a thickness, an index of refraction, an extinction coefficient, a linewidth of a latent image, a height of a latent image, a width of a feature, a height of a feature, overlay, or any combination thereof. A latent image generally refers to an image that may be formed in an exposed resist subsequent to a post exposure bake process.

The method may further include altering at least one parameter of a process module, configured to perform a step of the lithography process, in response to at least the one measured property of the resist. In this manner, within wafer variation of a critical metric may be reduced. The process module may include, but may not be limited to, a surface preparation module, a coat module, a bake module, an expose module, or a develop module. In addition, if at least one property of a resist disposed upon at least two wafers is measured, then the method may include altering at least one parameter of a process module in response to at least the one measured property of the resist disposed upon at least the two wafers. At least the one parameter may be altered using a feedback control technique, a feedforward control technique, an in situ control technique, or any combination thereof.

Altering at least the one parameter may include processing a first portion of a wafer with a first set of process conditions during the step and processing a second portion of the wafer with a second set of process conditions during the step. For example, if at least the one measured property includes thickness variation across the wafer, then a portion of the wafer coated with a thicker resist may be exposed with a higher exposure dose than a portion of the wafer coated with a thinner resist in response to the measured thickness variation. In an additional example, a portion of a wafer coated with a thicker resist may be heated to a higher temperature during a post exposure bake process than a portion of the wafer coated with a thinner resist in response to a measured thickness variation. In this manner, process conditions of a lithography process step may vary across a wafer such that a critical metric of the lithography process may be substantially uniform across the wafer despite variations in resist properties.

An additional embodiment relates to a system configured to reduce within wafer variation of a critical metric of a lithography process. The critical metric may include a critical dimension of a feature formed by the lithography process or any of the critical metrics as described above. The system may include at least one measurement device. At least the one measurement device may be configured to measure at least one property of a resist disposed upon a wafer during the lithography process. For example, at least the one measurement device may be configured to measure at least the one property of the resist at various locations across the wafer. In addition, at least the one measurement device may be configured to measure at least the one property of the resist between steps of the lithography process. Alternatively, at least the one measurement device may be configured to measure at least the one property of the resist during a step of the lithography process. For example, a measurement device may be integrated into a lithography cluster tool as described herein. Because a property of the resist may be measured during a lithography process, a method as described herein may have a quicker turn around time than conventional lithography process control methods. Therefore, a method as described herein may yield a larger number of semiconductor devices having relatively high performance bin characteristics. At least the one property may include any of the properties as described herein.

The system may also include a process module configured to perform a step of the lithography process. The process module may include, for example, a surface preparation module, a coat module, a bake module, an expose module, or a develop module. At least one parameter of the process module may be altered in response to at least the one measured property such that the within wafer variation of the critical metric may be reduced. In addition, at least the one parameter of the process module may be altered using a feedback control technique, a feedforward control technique, an in situ control technique, or any combination thereof. At least the one parameter of the process module may also be altered such that a first portion of the wafer can be processed with a first set of process conditions during the step and such that a second portion of the wafer can be processed with a second set of process conditions during the step.

The system may also include a controller computer coupled to at least the one measurement device and the process module. The controller computer may be configured to receive at least one measured property of the resist from the measurement device. The controller computer may also be configured to alter at least one parameter of the process module in response to at least the one measured property.

A further embodiment relates to a method for fabricating a semiconductor device. For example, the method may include measuring at least one property of a resist disposed upon a wafer during a lithography process. The method may also include altering at least one parameter of at least one process module in response to at least the one measured property of the resist to reduce within wafer variation of a critical metric of the lithography process. In addition, the method may include processing the wafer to form at least a portion of at least one semiconductor device upon the wafer. For example, processing the wafer may include etching, ion implantation, deposition, chemical mechanical polishing, or plating. In this manner, semiconductor devices formed by the method may have higher performance bin distributions thereby improving not only yield but also high margin product yield.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
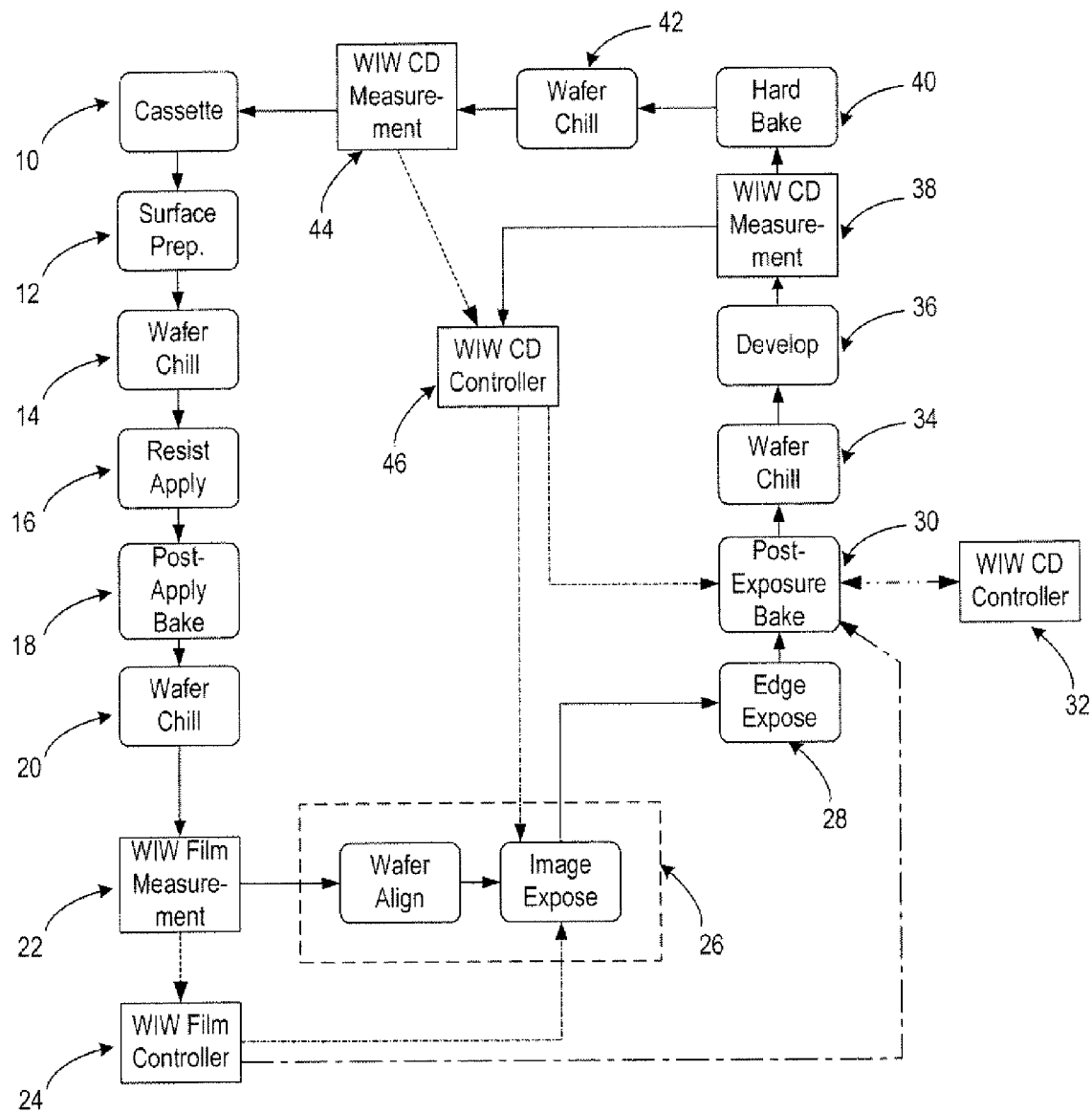
FIG. 1 depicts a flow chart illustrating a method for evaluating and controlling a lithography process.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, FIG. 1 illustrates an embodiment of a method to evaluate and control performance characteristics of a lithography process. For example, the method may be used to reduce, and even to minimize, within wafer ("WIW") variability of critical metrics of the lithography process. Critical metrics of a lithography process may include, but are not limited to, critical dimensions of features formed by the lithography process and overlay. Critical dimensions of features formed during the lithography process may include, for example, a width, a height, and a sidewall profile of the features. A sidewall profile of a feature may be described, for example, by a sidewall angle of the feature with respect to an upper surface of a wafer, a roughness of the sidewall of the feature, and other physical characteristics of the feature. Overlay generally refers to a lateral position of a feature on one level of a wafer with respect to a lateral position of a feature on another level of the wafer. The lithography process may include optical lithography, e-beam lithography, or x-ray lithography.

Figure 3:
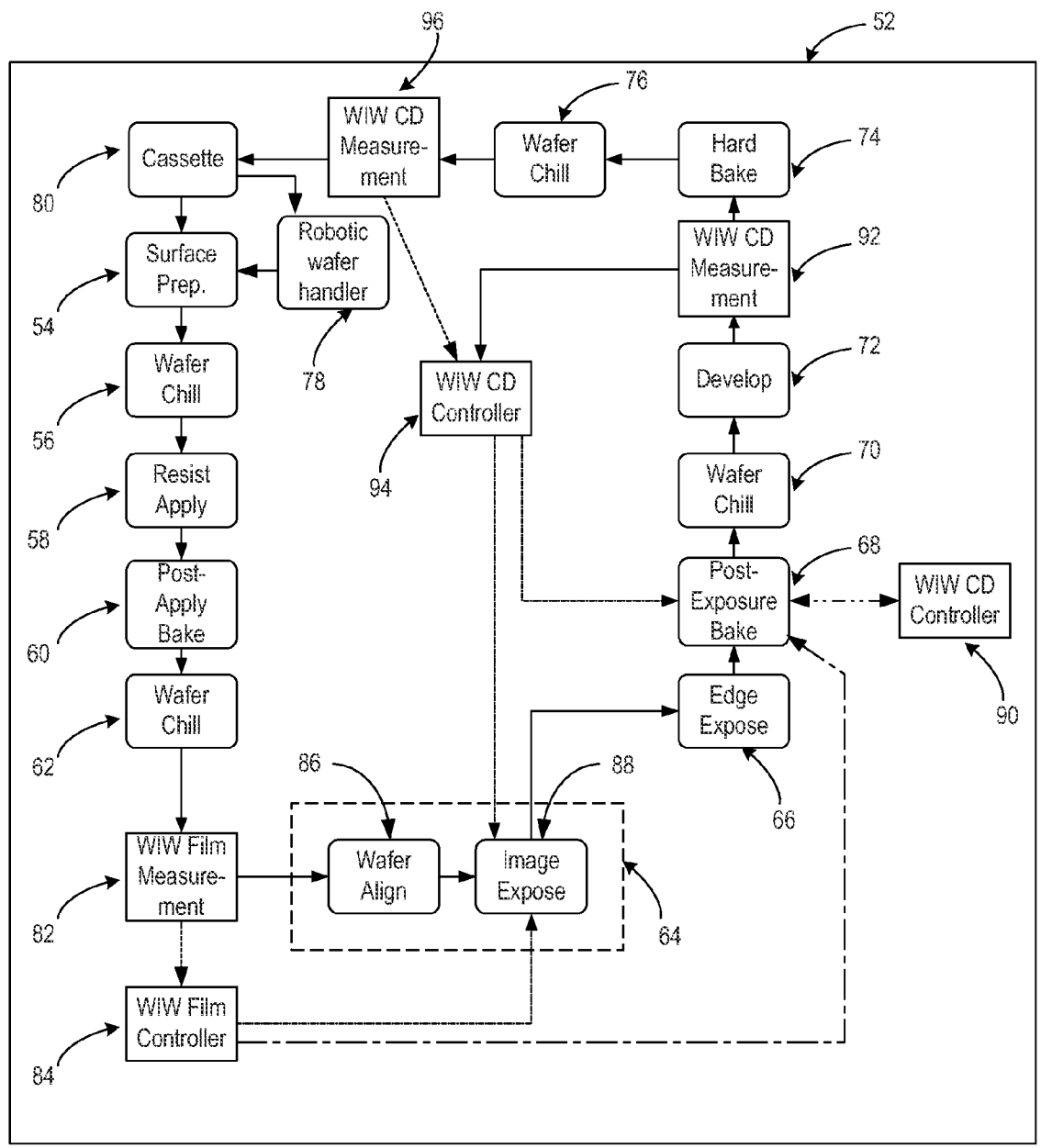
FIG. 3 depicts a block diagram of a system configured to evaluate and control a lithography process.

A lithography cluster tool, or a lithography track, (e.g., lithography cluster tool 52 shown in FIG. 3) may include a set of process modules (e.g., surface preparation chamber 54, wafer chill module 56, resist apply process module 58, post apply bake module 60, wafer chill module 62, exposure process module 64, edge exposure module 66, post exposure bake module 68, wafer chill module 70, develop module 72, hard bake module 74, and wafer chill module 76 shown in FIG. 3). An example of a lithography cluster tool is illustrated in U.S. Pat. No. 5,968,691 to Yoshioka et al., and is incorporated by reference as if fully set forth herein. The lithography cluster tool may be coupled to an exposure tool. A first portion of the process modules may be configured to perform at least one step of the lithography process prior to exposure of the resist. A second portion of the process modules may be configured to perform process steps of the lithography process subsequent to exposure of the resist. The lithography cluster tool may also include at least one robotic wafer handler (e.g., robotic wafer handler 78 shown in FIG. 3). The robotic wafer handler may move wafers from module to module. The robotic wafer handler may also be used to move wafers from the lithography cluster tool to the exposure tool.

As shown in step 10, the robotic wafer handler may pick up a wafer from a cassette (e.g., cassette 80 shown in FIG. 3), which may be loaded into the lithography cluster tool by an operator. The cassette may contain a number of wafers which may be processed during the lithography process. The wafers may be bare silicon wafers. Alternatively, the wafers may have been processed prior to the lithography process. For example, topographical features may have been formed on the wafers. The topographical features may include trenches, vias, lines, etc. In addition, one or more layers of a material such as a dielectric material may have been formed on the wafers prior to the lithography process.

The wafer may be placed in a process module such as a surface preparation chamber, as shown in step 12. The surface preparation chamber may be configured to form a layer of an adhesion promoting chemical such as hexamethyldisilazane ("HMDS") onto the surface of the wafer. HMDS may be deposited at a temperature of approximately 80° C. to approximately 180° C. Therefore, after the surface preparation process, the robotic wafer handler may remove the wafer from the surface preparation chamber and may place the wafer into a chill module, as shown in step 14. As such, a wafer may be lowered to a temperature suitable for subsequent processing (e.g., approximately 20° C. to approximately 25° C.).

In an additional embodiment, an anti-reflective coating may also be formed on the surface of the wafer. The anti-reflective coating may be formed on the wafer, for example, by spin coating followed by a post apply bake process. Since a post apply bake process for an anti-reflective coating generally involves heating a coated wafer to a temperature of approximately 175° C. to approximately 230° C., a chill process may also be performed subsequent to the post apply bake process.

A resist may be formed upon the wafer, as shown in step 16. For example, the wafer may be placed into a resist apply process module. A resist may be automatically dispensed onto an upper surface of the wafer. The resist may be uniformly distributed across the wafer by spinning the wafer at a high rate of speed such as about 2000 rpm to about 4000 rpm. The spinning process may adequately dry the resist such that the wafer may be removed from the resist apply module without affecting the coated resist. As shown in step 18, the resist-coated wafer may be heated in a post apply bake process. The post apply bake process may include heating the resist-coated wafer at a temperature of approximately 90° C. to approximately 140° C. The post apply bake process may be used to drive excess solvent out of the resist and to alter a property of an upper surface of the resist such as surface tension. Subsequent to the post apply bake process, the wafer may be chilled at a temperature of approximately 20° C. to approximately 25° C., as shown in step 20.

The method may also include measuring a property of the resist formed upon the wafer subsequent to chilling. As shown in step 22, for example, the wafer may be moved to a measurement device, or a within wafer film measurement device (e.g., within wafer film measurement device 82 shown in FIG. 3), subsequent to chilling after the post apply bake step. Alternatively, the wafer may remain in the chill module during measurement if, for example, the measurement device is coupled to the chill module. The measurement device may be any device configured to use an optical technique to measure at least one property of the resist. The measurement device may also be configured to measure at least one property of the resist at more than one position on the wafer. The optical technique may include, but is not limited to, scatterometry, interferometry, reflectometry, spectroscopic ellipsometry or spectroscopic reflectometry. Additionally, other optical measurement devices may also be used to measure a property of the resist. Examples of measurement devices which may be used are illustrated in U.S. Pat. No. 4,999,014 to Gold et al., U.S. Pat. No. 5,042,951 to Gold et al., U.S. Pat. No. 5,412,473 to Rosencwaig et al., U.S. Pat. No. 5,516,608 to Hobbs et al., U.S. Pat. No. 5,581,350 to Chen et al., U.S. Pat. No. 5,596,406 to Rosencwaig et al., U.S. Pat. No. 5,596,411 to Fanton et al., U.S. Pat. No. 5,608,526 to Piwonka-Corle et al., U.S. Pat. No. 5,747,813 to Norton et al., U.S. Pat. No. 5,771,094 to Carter et al., U.S. Pat. No. 5,798,837 to Aspnes et al., U.S. Pat. No. 5,859,424 to Norton et al., U.S. Pat. No. 5,877,859 to Aspnes et al., U.S. Pat. No. 5,889,593 to Bareket et al., U.S. Pat. No. 5,900,939 to Aspnes et al., U.S. Pat. No. 5,910,842 to Piwonka-Corle et al., U.S. Pat. No. 5,917,588 to Addiego, U.S. Pat. No. 5,917,594 to Norton, U.S. Pat. No. 5,973,787 to Aspnes et al., and U.S. Pat. No. 5,991,699 to Kulkarni, et al. and are incorporated by reference as if fully set forth herein. Additional examples of measurement devices are illustrated in PCT Application No. WO 99/02970 to Rosencwaig et al. and PCT Application No. WO 99/45340 to Xu et al., and are incorporated by reference as if fully set forth herein.

Figure 4:
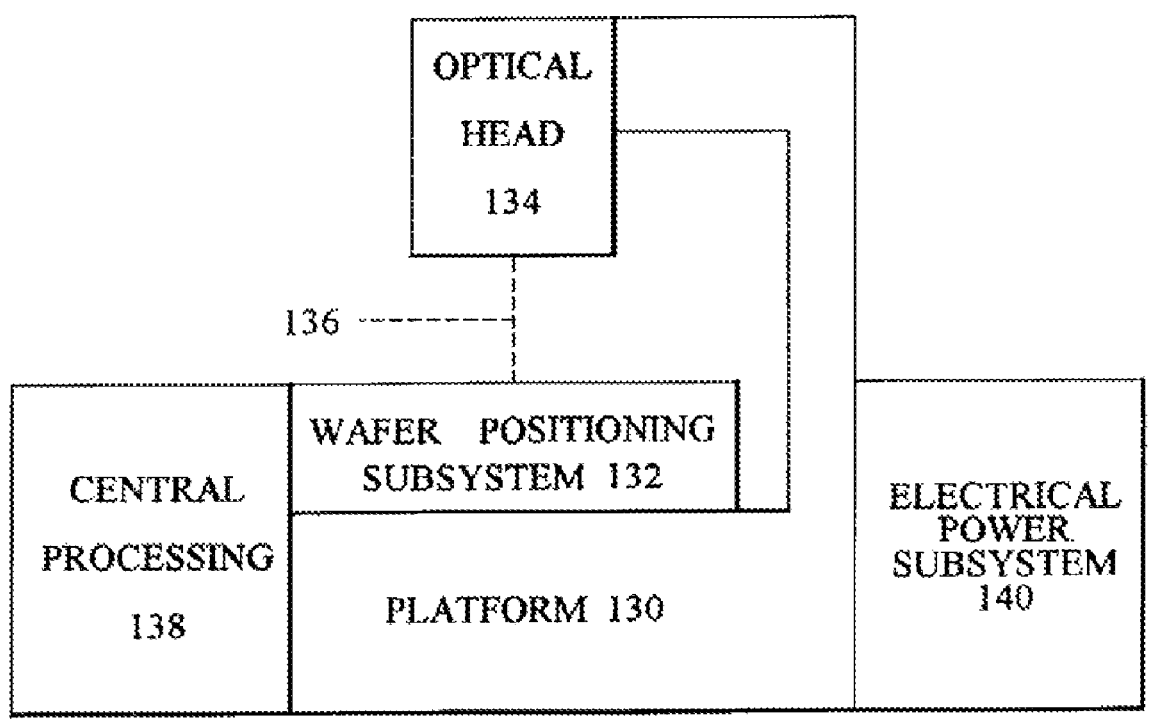
FIG. 4 is a side view block diagram showing a measurement device that may be used in the embodiments described herein.

With reference to FIG. 4, a practical apparatus for semiconductor wafer metrology integrates an angle-dependent reflectometer within a machine that automates the measurement process. The apparatus can repeat the desired measurement or measurements at many pre-programmed locations on a wafer, and on many wafers, at a high rate with minimal intervention on the part of a human operator. The apparatus includes a platform 130, which is a stable table that provides isolation from floor vibrations by means of springs or pneumatic isolators. The platform 130 holds a wafer positioning subsystem 132 and an optical head 134 containing the reflectometer. Relative motion between those two elements 132 and 134 is held by the platform 130 during measurements to less than 2 to 5 micrometers. The platform 130 can also include means for moving the optical head 134 up and down relative to the wafer positioning assembly 132 to allow for unobstructed loading or unloading of a wafer by a wafer handler and also to provide coarse focusing in order to accommodate wafers of various thicknesses.

The apparatus' wafer positioning subsystem 132 includes or cooperates with wafer handling equipment for loading and unloading wafers onto the machine. The wafer handling equipment includes one or more wafer storage cassettes and an autoloader assembly that moves wafers between the storage cassettes and a stage. The autoloader usually forms an integral part of the overall instrument. The cassettes are typically provided separately. The wafer positioning subsystem 132 further includes a stage assembly with a vacuum chuck that holds a wafer securely and a combination of motors and slides that produce precise motion of the stage in at least two, and preferably three, axes. Fine z-axis motion (up and down), if not provided by the stage, can be provided by the optical head 134. The stage may also provide for rotational motion of the wafer.

Wafer positioning is the result of cooperation between the wafer positioning subsystem 132, a wafer alignment sensor in the optical head 134, and motion control provided by a central processing system 138. The alignment sensor is a low magnification (about 1× to 6×) camera that images a small illuminated area of a semiconductor die on the wafer. A motion control processor in the central processing system 138 receives image data from the alignment sensor, employs pattern recognition algorithms to identify unique alignment marks or recognizable pattern features on the wafer, and then controls the motion motors of the stage to automatically position the wafer at an initial point and align it with the axes of motion. The wafer can then be navigated to designated measurement positions for that wafer. A template matching technique like that described by Ramesh Jain, et al. in the book Machine Vision, published by McGraw-Hill Inc. (1995), section 15.6.1, pages 482-483, can be used to recognize a wafer's alignment mark. Measurement points relative to an initial wafer position can be designated by a user for a particular class of wafers to be inspected.

The optical head 134 is in optical communication 136 with the wafer on the positioning subsystem's stage. In addition, it includes the wafer alignment sensor (camera) that aids the wafer positioning subsystem 132. Further, the optical head 134 includes a focus sensor that enables automatic focusing. One commonly used focus sensor uses a light source that is focused on the wafer surface at an angle. The reflected light is detected by a bi-cell detector. As the focus varies, the detected beam will translate across the bi-cell. This type of autofocus system is described by D. H. Kim et al. in Proceedings SPIE, vol. 2726, pages 876-885 (1996). The three optical head elements, reflectometer, alignment sensor and autofocus sensor, are not optically integrated, but are physically mounted together within a single unit and have a common focus condition. While the alignment sensor normally images a slightly different location than the spot illuminated by the reflectometer, the lateral displacement is fixed and can be taken into account when positioning the wafer for measurement. Likewise, even if the autofocus sensor were to use a slightly different location on the wafer for determining the focus condition, the wafer is sufficiently flat that focus would be within the required focus tolerance for the reflectometer.

An electrical power subsystem 140 includes one or more power supplies and distribution cables to provide AC and DC power to the electronic components and motion motors of the apparatus.

The central processing system 138 includes one or more computer processors for digital motion control of the wafer positioning system 132 stage and of the optical head 134 and for data acquisition and analysis. For example, there may be several processors which are each dedicated to a particular function and a main or host processor for coordinating the separate processors. Moreover, there may be one or more data ports and a network interface processor for possible interaction via a network with a factory computer. The central processing system 132 also includes memory for storing designated measurement locations as well as actual measurement data and the analysis results. The system shown in FIG. 4 may be further configured as described in U.S. Pat. No. 5,889,593 to Bareket, which is incorporated by reference above.

Figure 5:
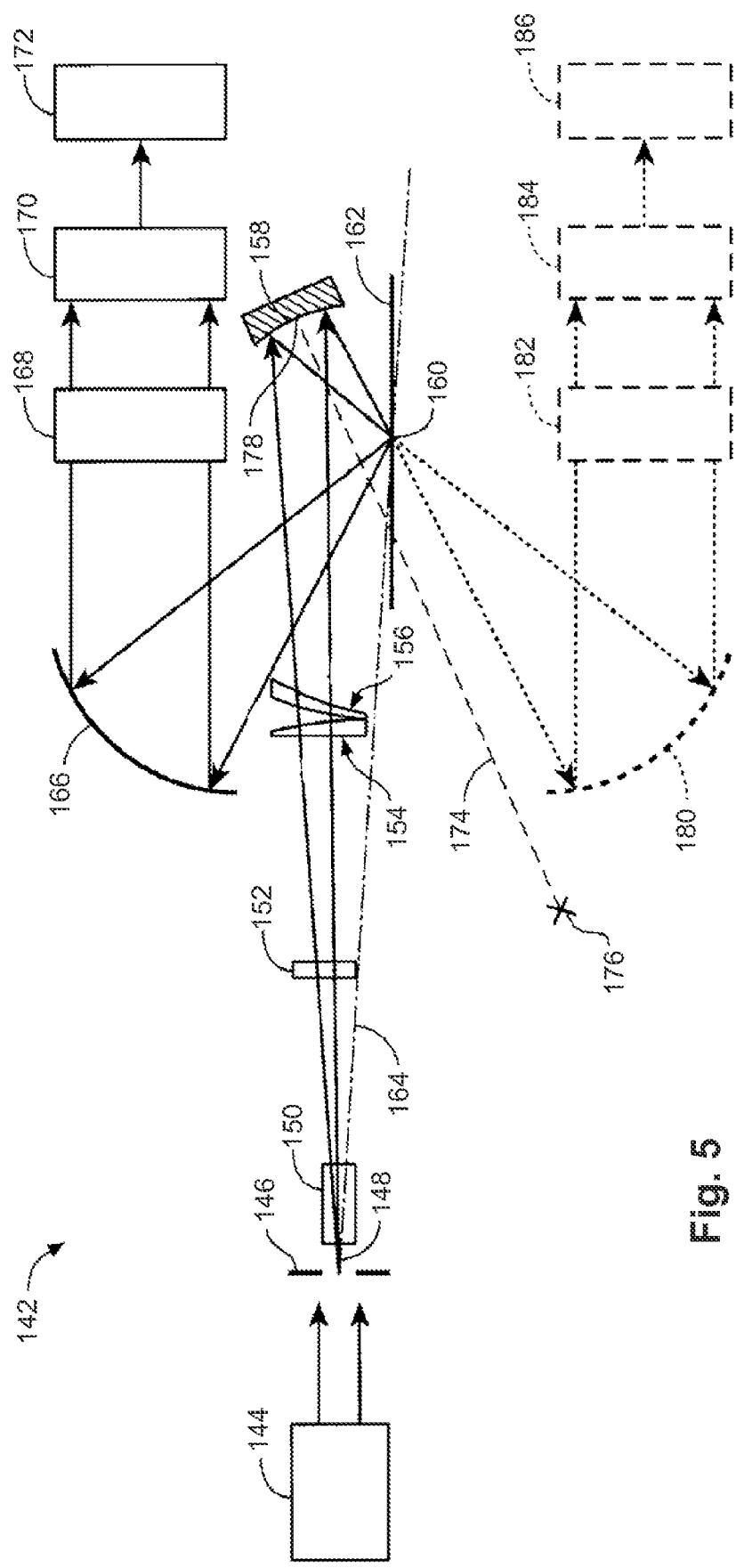
FIG. 5 is a schematic diagram of a measurement device that may be used in the embodiments described herein.

FIG. 5 illustrates a measurement device that may be used in embodiments described herein. In reference to system 142 of FIG. 5, a broadband radiation source (preferably a xenon arc lamp) 144 supplies radiation through an aperture 146 along an optical path 148 to a polarizer 150. Polarizer 150 polarizes the radiation and the polarized radiation is passed through an apodizer 152 which also acts as an aperture stop for the system 142. The beam from apodizer 152 is passed through lens 154 and 156 to a spherical mirror 158 which focuses the radiation onto a small spot 160 on the surface of sample 162. An image of the aperture is thus focused onto an image plane at the spot 160, and the dotted line 164 connecting the aperture and the spot is the optical axis of system 142. The radiation reflected from sample 162 is collected by a collection mirror 166 which focuses the collected light to an analyzer 168 and a spectrometer 170 with its associated aperture (not shown). The output of the spectrometer is analyzed by a computer 172 to determine the change in amplitude and phase of polarization caused by interaction of the sampling beam with the sample.

By replacing an ellipsoidal mirror of U.S. Pat. No. 5,608,526 with a spherical mirror as in FIG. 5, the limiting factor of errors produced by diamond turning is eliminated and the minimum box size within which accurate ellipsometric measurements can be made is no longer so limited. The box size achieved in this invention can be 40 by 40 microns or smaller. In the preferred or other embodiments, a polarizer and an analyzer can include any element that modifies the polarization of radiation, such as a linear polarizer and a wave plate or an acousto-optic modulator. The axis 174 of the mirror may be defined with respect to its center of curvature 176 and center 178 of the illuminated area on the mirror in the preferred embodiment as shown in FIG. 5.

Instead of collecting and detecting radiation that is reflected by a sample 162, where the sample transmits radiation, it is also possible to detect radiation that is transmitted through the sample, such as by means of mirror 180, which focuses the collected radiation to analyzer 182 and spectrometer 184 and computer 186, shown in dotted lines in FIG. 5, and to thereby determine the change in amplitude and phase of polarization caused by interaction of the sampling beam with the sample. In still other variations, it may be possible to collect radiation that is scattered by or through the sample to determine the change in amplitude and phase of polarization caused by interaction of the sampling beam with the sample. The system shown in FIG. 5 may be further configured as described in U.S. Pat. No. 5,917,594 to Norton, which is incorporated by reference above.

The measurement device may measure at least one property of the resist. In addition, the measurement device may measure several properties of the resist substantially simultaneously. A property of the resist measured subsequent to a post apply bake process may include, but is not limited to, a thickness, an index of refraction, or an extinction coefficient of the resist. The measured property may be sent to a controller computer, or a within wafer film controller (e.g., within wafer film controller 84 shown in FIG. 3), as shown in step 24 of FIG. 1. The controller computer may be coupled to the measurement device. The controller computer may determine a parameter of a process step of the lithography process in response to the measured property of the resist. For example, the controller computer may determine a parameter of a process step as a function of the resist using an experimentally determined or numerically simulated relationship. The controller computer may also be coupled to at least one process module of the lithography cluster tool. In this manner, the controller computer may be configured to alter a parameter of a process module of a lithography cluster tool. Therefore, the controller computer may control the operation of any of the process modules included in the lithography cluster tool. Alternatively, a parameter of a process module may be altered manually by an operator in response to output from the measurement device or the controller computer.

In an embodiment, a feedforward control technique may be used to alter a parameter of a process module. For example, an operator or a controller computer may determine at least one parameter of a process module that may be used to perform an additional lithography process step on the measured resist. Additional lithography process steps may include exposure and post exposure bake. In this manner, the property of the resist may be used to alter a parameter of a process module configured to perform an exposure step or a post exposure bake step. For example, a thickness, an index of refraction, and/or an extinction coefficient of the resist measured subsequent to the chilling process may be used to determine an exposure dose of an exposure process or a temperature of the post exposure bake process. An operator or the controller computer may alter at least one parameter of the exposure process module or the post exposure bake process module in response to the determined exposure dose or temperature, respectively.

In addition, because at least one property of the resist may be measured at various positions across the wafer, at least one parameter may be determined for each of the various positions. As such, a parameter of a process module may also be altered, as described above, independently from field to field on the wafer. For example, process conditions such as exposure dose and/or post exposure bake temperature may vary across the wafer in subsequent processes in response to variations in at least one measured property from field to field across the wafer. In this manner, critical metrics of the lithography process may be substantially uniform across the wafer.

In an additional embodiment, a feedback control technique may be used to alter a parameter of a process module. In this manner, a parameter of at least one process module that may have been used to form the resist may be altered prior to or during processes to form resist on additional wafers. Such a parameter may be determined in response to at least the one measured property of the resist as described above. For example, the property of the resist may be used to alter a parameter of the resist apply process module or the post apply bake process module prior to and/or during processing of additional wafers.

As shown in step 26, the wafer may be transferred to an exposure process module. The exposure process module may perform a number of operations that may include, but are not limited to, aligning a wafer (e.g., using wafer align module 86 shown in FIG. 3) and exposing the resist in a predetermined pattern (e.g., using image expose module 88 shown in FIG. 3). For example, the exposure process module may include any stepper or scanner known in the art. Exposing the resist may also include exposing the resist to a specific intensity of light, or an exposure dose, and a specific focus condition. Many exposure process modules may be configured such that the exposure dose and focus conditions of the expose process may be varied across the wafer, for example, from field to field. The exposure dose and focus conditions may be determined and/or altered as described herein using a feedback or feedforward control technique.

As shown in step 28, an optional process step in the lithography process may include an edge exposure step. The edge exposure step may include exposing resist disposed proximate an outer edge of the wafer to a light source to remove the resist at the outer edge of the wafer. Such removal of the resist at the outer edge of a wafer may reduce contamination of process chambers and devices used in subsequent processes.

As shown in step 30, the wafer may be subjected to a post exposure bake process step. The post exposure bake process may be used to drive a chemical reaction in exposed portions of the resist such that portions of the resist may be removed in subsequent processing. As such, the performance of the post exposure bake process may be critical to the performance of the lithography process. The post exposure bake process may include heating the wafer to a temperature of approximately 90° C. to approximately 150° C. As shown in step 32, a measurement device, or a within wafer critical dimension measurement device (e.g., within wafer CD controller 90 shown in FIG. 3), may be coupled to the post exposure bake process module. In this manner, a property of the resist may be measured during the post exposure bake process. The measurement device may use an optical technique to measure a property of the resist such as thickness, linewidth of a latent image, height of a latent image, index of refraction, or extinction coefficient. The measurement device may be configured to use a technique such as scatterometry, interferometry, reflectometry, spectroscopic ellipsometry, and spectroscopic reflectometry. Additional examples of measurement devices may include any of the measurement devices as described herein. Therefore, the measured property of the resist may be used to evaluate and control the post exposure bake process using an in situ control technique. For example, the measurement device may measure a property of the resist during the post exposure bake process, and a parameter of the post exposure bake process module may be altered in response to the measured property during the process.

In addition, the measurement device may be used to measure a property of the resist at various times during a post exposure bake process. As such, the measurement device may monitor variations in at least one property of the resist over time. In this manner, a signature characteristic of an endpoint of the post exposure bake process may be determined, and at which time, the process may be ended. Monitoring variations in at least one property of the resist during the post exposure bake process may also be enhanced by measuring at least one property of the resist at multiple positions on the wafer.

The measurement device may be configured to measure a property of the resist at multiple positions within a field and at multiple positions within at least two fields on the wafer during the post exposure bake process. In this manner, at least one parameter of the process module may be determined at various positions across the wafer. As such, a parameter of the post exposure bake module may be altered independently as described above from field to field on the wafer. For example, a temperature of a bake plate of the post exposure bake process module may vary across the bake plate during the post exposure bake process in response to variations in at least one measurement property of the resist from field to field across the wafer. Therefore, within wafer variations of critical parameters may be reduced, or even minimized.

Figure 2:
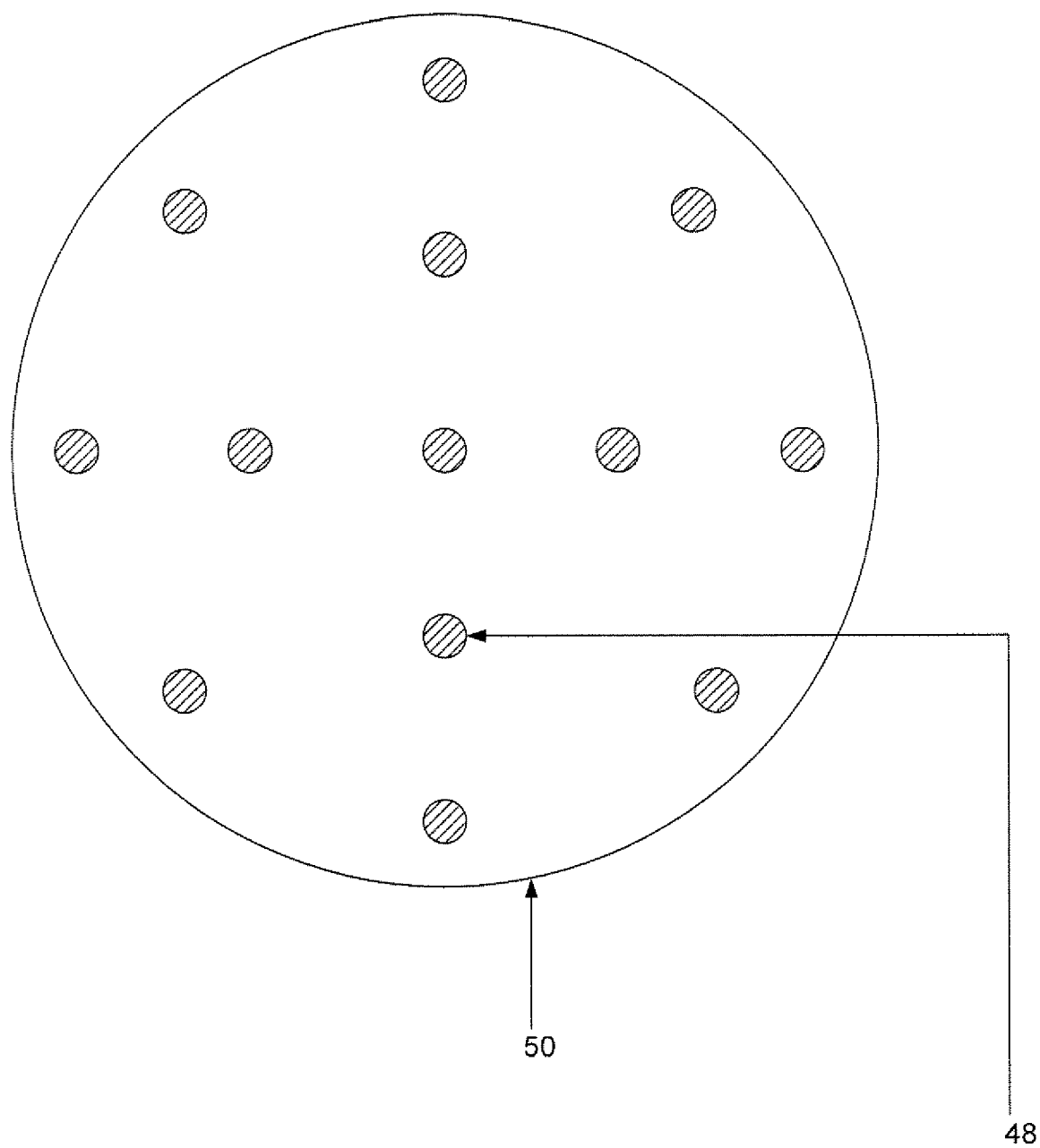
FIG. 2 depicts a plan view of a bake plate of a post exposure bake process module having a number of discrete secondary heating elements in addition to an overall primary heating element.

As shown in FIG. 2, a temperature of the post exposure bake plate may be altered across the bake plate by using a number of discrete secondary heating elements 48 disposed within primary heating element 50. Secondary heating elements 48 and primary heating element 50 may include resistive heating elements or any other heat source known in the art. Secondary heating elements 48 may be independently controlled, for example, by altering an electrical current supplied to each of the secondary heating elements to alter a temperature profile of primary heating element 50. As such, a temperature profile across a wafer during a post exposure bake process may be altered such that individual fields on a wafer may be heated at substantially the same temperature or at individually determined temperatures. In this manner, a uniformity of critical metrics of a lithography process across a wafer may be increased.

Referring to FIG. 1 again, as shown in step 34, subsequent to the post exposure bake process, the wafer may be chilled. Subsequent to chilling, the wafer may be moved to a measurement device. Alternatively, the wafer may remain in the chill module during measurement if, for example, the measurement device is coupled to the chill module. The measurement device may be configured as any measurement device as described herein. The measurement device may measure at least one property of the resist. In addition, the measurement device may measure several properties of the resist substantially simultaneously. A property of the resist measured subsequent to or during the chill process may include, but is not limited to, a thickness, a linewidth of a latent image, a height of a latent image, an index of refraction, or an extinction coefficient. The measured property of the resist may be used to alter a parameter of a process module of the lithography cluster tool using a feedback control technique or a feedforward control technique. For example, the measured property of the resist may be used to alter an exposure dose or a post exposure bake temperature using a feedback control technique or to alter a develop time using a feedforward control technique.

The measurement device may be configured to measure a property of the resist at multiple positions within a field and at multiple positions within at least two fields on the wafer subsequent to or during the chill process. In this manner, at least one parameter of a process module of a lithography cluster tool may be determined at various positions across the wafer. As such, a parameter of an exposure process module, a post exposure bake process module, or a develop process module may be altered independently as described above from field to field on the wafer. For example, a temperature of a bake plate of the post exposure bake process module may vary across the bake plate in response to variations in at least one measurement property of the resist from field to field across the wafer. As described above, therefore, within wafer variations of critical parameters may be reduced, or even minimized.

As shown in step 36, subsequent to the post exposure process, the wafer may be subjected to a develop process step. The develop process step may be configured to remove a portion of the resist. For example, a develop process may include dispensing an aqueous developer solution on a wafer subsequent to a post exposure bake process and rinsing the wafer with de-ionized water. Resist remaining after the develop process step may define a pattern formed in the original resist layer. The formed pattern may include an arrangement of lines, spaces, trenches, and/or vias. Subsequent to the develop process, as shown in step 38, a measurement device, or a within wafer critical dimension measurement device (e.g., within wafer critical dimension measurement device 92 shown in FIG. 3), may be used to measure a property of the resist such as, but not limited to, a thickness, an index of refraction, or an extinction coefficient of the remaining resist, a width, a height, or a sidewall profile of a feature, or overlay. The measured property may be sent to a controller computer, or within wafer critical metric controller (e.g., within wafer critical dimension controller 94 shown in FIG. 3), as shown in step 46 of FIG. 1.

A parameter of a process module involved in the lithography process may be altered in response to the measured property using a feedback control technique. For example, the altered parameter of the process module may be a function of the measured property of the resist. The feedback control technique may include, for example, measuring a linewidth of features formed in the resist subsequent to the develop process step and altering a parameter of an expose process module or a post exposure bake process module, which may be used to fabricate additional wafers. In addition, a linewidth of features formed in the resist may be measured at various positions across the wafer subsequent to the develop process step. In this manner, parameters of an expose process module may be altered at the field level in response to the measured properties of the resist by altering parameters of the expose process step such as the exposure dose and the exposure focus conditions at each field. As such, the controller computer may provide a two-dimensional array of exposure doses and/or exposure focus conditions to the exposure process module in response to the measured property of the resist. Therefore, variations in wafer critical metrics of the lithography process may be reduced, or even minimized.

As shown in step 40, subsequent to measuring a property of the resist, a hard bake, or post develop bake, process step may be performed. The hard bake process may be used to drive contaminants and any excess water from the resist. Therefore, the hard bake process may include heating the wafer at a temperature of approximately 90° C. to approximately 130° C. As shown in step 42, the temperature of the wafer may then be reduced by using a wafer chill process. Subsequent to the wafer chill process of step 42, an additional measurement of at least one property of the resist may be performed as described herein, as shown in step 44. The measurement device (e.g., within wafer critical dimension measurement device 96 shown in FIG. 3) may be configured as described in any of the above embodiments. This measurement may also be used to alter a parameter of a process module using a feedback control technique as described herein. For example, at least one measured property of a resist may be sent to a controller computer, or a within wafer critical dimension controller, as shown in step 46.

It is to be understood that all of the measurements described above may be used to alter a parameter of a lithography process module using a feedback, a feedforward, or an in situ process control technique. In addition, within wafer variations of critical metrics of a lithography process may be further reduced by using a combination of the above techniques. The method may also include measurements at additional points in a lithography process such as measuring at least one property of an anti-reflective coating subsequent to forming the anti-reflective coating on a wafer. The property of the anti-reflective coating may be used to alter a parameter of a process module using a feedback control technique, a feedforward control technique, or an in situ control technique as described herein.

In an additional embodiment, a system configured to evaluate and control a lithography process may include at least one measurement device and at least one process module. The system may be configured to reduce, and even to minimize, within wafer variability of at least one critical metric of the lithography process. Critical metrics of a lithography process include, but are not limited to, critical dimensions of features formed by the lithography process and overlay as described above.

A measurement device may be configured to measure at least one property of a resist disposed upon a wafer during the lithography process. As shown in FIG. 1, for example, a measurement device may include within wafer film measurement device 22, within wafer critical dimension measurement device 32, within wafer critical dimension measurement device 38, and/or within wafer critical dimension measurement device 44. Such measurement devices may be configured as described herein. In addition, the system may include additional measurement devices as described herein. The measurement device may be configured to measure the property of the resist during any of the process steps as described above or subsequent to any of the process steps as described above.

In an embodiment, therefore, the measurement device may be coupled to at least one of the process modules such that the measurement device may perform an in situ measurement of a resist. Alternatively, the measurement device may be disposed within a lithography cluster tool such that the measurement device may perform a measurement of a resist between two process steps. In this manner, a method as described herein may have a quicker turn around time than conventional lithography process control methods. As described herein, at least the one measured property may include a thickness, an index of refraction, an extinction coefficient, a linewidth of a latent image, a height of a latent image, a width of a feature, a height of a feature, a sidewall profile of a feature, overlay, or any combination thereof. At least the one measurement device may also be configured to measure at least the one property of the resist at various locations across the wafer. For example, a thickness of the resist may be measured at various positions or fields across the wafer. In addition, a property of the resist may be measured at various positions within a field of the wafer or at various positions within several fields of the wafer.

A process module may be configured to perform a step of the lithography process. As shown in FIG. 1, for example, such process modules may include, but are not limited to, surface preparation chamber 12, resist apply process module 16, post apply bake process module 18, exposure process module 26, post exposure bake process module 30, develop process module 36, and hard bake process module 40. At least one parameter of the process module may be altered in response to at least the one measured property such that within wafer variation of the critical metric can be reduced, or even minimized. For example, at least one parameter of a process module may be altered using a feedback control technique, a feedforward control technique, an in situ control technique, or any combination thereof.

In addition, at least the one parameter of the process module may be altered such that a first portion of the wafer may be processed with a first set of process conditions during a step of the lithography process and such that a second portion of the wafer may be processed with a second set of process conditions during the step. For example, each portion of the wafer may be a field of the wafer. In this manner, each field of the wafer may be subjected to different process conditions such as, but not limited to, exposure dose and focus conditions and post exposure bake temperatures. As such, because each field of a wafer may be subjected to process conditions that may vary depending upon a measured property of a resist formed upon the wafer, within wafer variations in critical metrics of the lithography process may be substantially reduced, or even minimized.

The system may also include a controller computer coupled to at least one measurement device and to at least one process module. As shown in FIG. 1, for example, a controller computer may include within wafer film controller 24 and within wafer critical dimension controller 46. The controller computer may include any appropriate controller device known in the art. The controller computer may be configured to receive at least one measured property of the resist from the measurement device. In addition, the controller computer may be configured to determine at least one parameter of a process module in response to the measured property of the resist. For example, the controller computer may be configured to use an experimentally determined or a numerically simulated relationship between the property and the parameter to determine a parameter in response to the property. The controller computer may be further configured to control the process module such that the parameter may be altered in response to the determined parameter. Therefore, the altered parameter of the process step may be a function of at least one measured property of the resist. The controller computer may also be configured to control the measurement device to measure the physical property of the resist.

In an additional embodiment, the system may be configured to monitor variations in at least one property of the resist. For example, a measurement device may be configured to measure a property of the resist substantially continuously or at predetermined time intervals during a step of the lithography process. A controller computer coupled to the system may, therefore, receive the measured property from the measurement device and may monitor variations in the property over the duration of a process step of the lithography process. By analyzing the variations in at least one property of the resist during a step of the lithography process, the controller computer may also generate a signature representative of a process step such as a post exposure bake process. The signature may include at least one singularity which may be characteristic of an endpoint of the post exposure bake process. An appropriate endpoint for the process step may be a linewidth or a thickness of a latent image in the resist formed during the post exposure bake process. The linewidth or the thickness of the latent image may be larger or smaller depending upon the semiconductor device feature being fabricated by the lithography process. After the controller computer may have detected the singularity of the signature, the controller computer may stop the post exposure bake process by altering a level of a parameter of an instrument coupled to the post exposure bake process module.

In an embodiment, a method for fabricating a semiconductor device may include a lithography process in which a pattern may be transferred from a reticle to a resist. For example, portions of the resist may be removed using a lithography process such that regions of the wafer or an underlying layer may be exposed to a subsequent process such as an ion implantation process. The predetermined regions may be regions of the wafer or the underlying layer in which features of a semiconductor device are to be formed such as, for example, source/drain junctions. Fabricating a semiconductor device may also include evaluating and controlling a lithography process by measuring at least one property of a resist disposed upon a wafer during the lithography process. In addition, measuring at least one property of the resist may include measuring within wafer variations in at least one property of the resist during the lithography process. The physical property of the resist may be altered by a process step of the lithography process.

The method for fabricating a semiconductor device may also include determining and/or altering at least one parameter of a process module which may be configured to perform a step of the lithography process. The altered parameter may be determined in response to at least one measured property of the resist to reduce within wafer variations of a critical metric of the lithography process. For example, the altered parameter may be determined using a function which describes a relationship between the physical property of the resist and a parameter of the process step of the lithography process. The altered parameter may also be determined independently at various positions within a field or within several fields of the wafer. In this manner, semiconductor devices fabricated by the method may have higher performance bin distributions thereby improving not only yield but also high margin product yield. In addition, the method for fabricating a semiconductor device may include processing a wafer to form at least a portion of at least one semiconductor device upon the wafer. For example, processing the wafer may include at least one semiconductor fabrication process such as etching, ion implantation, deposition, chemical mechanical polishing, plating, and/or any other semiconductor fabrication process known in the art.

A set of data may be collected and analyzed that may used to determine a parameter of a process module in response to a measured property of a resist formed upon a wafer. Process control methods as described herein may also be used to further optimize a lithography process by using optical measurements as described herein in conjunction with electrical measurements of a semiconductor device that may be formed with the lithography process. The combination of optical and electrical measurements may provide a larger amount of characterization data for a lithography process. In this manner, the characterization data may be used to understand the mechanisms of lithography, to pin-point the cause of defects, and to make accurate adjustments to parameters of various process modules, or the process conditions. In addition, such a process control strategy may be used to qualify, or characterize the performance of, a new lithography tool. The process control method may also be used to compare the performance of several similar lithography tools. Such a comparison may be used, for example, in a manufacturing environment in which several tools may be used in parallel to manufacture one device or product. Furthermore, this process control strategy may be used to determine an appropriate resist and thickness in the development stages of defining a lithography process.

In an embodiment, a quantitative relationship may be developed between a parameter of a process module that may be varied and a property of a resist. For example, a number of wafers may be processed using variations of a parameter of the process module. All other parameters of the process module and additional process modules may remain constant, and a correlation between the varied parameter and a property of the resist may be developed. In this manner, an algorithm that describes the quantitative relationship between each of the process parameters for a process module and the measured property of the resist may be determined. The developed algorithms may be used during processing of product wafers to determine if the process is operating within design tolerance for a process and a process module. Additionally, algorithms may be developed and used to further optimize a current process, to characterize a new process module, or to develop processes to fabricate next generation devices.

Furthermore, this algorithm may be integrated into a controller for a measurement device or a process module. The controller may by a computer system configured to operate software to control the operation of a measurement device such as a scatterometer, an interferometer, a reflectometer, a spectroscopic ellipsometer, or a spectroscopic reflectometer. The computer system may include a memory medium on which computer programs for operating the device and performing calculations related to the collected data. The term "memory medium" is intended to include an installation medium. e.g., a CD-ROM, or floppy disks, a computer system memory such as DRAM, SRAM, EDO RAM, Rambus RAM, etc., or a non-volatile memory such as a magnetic media, e.g., a hard drive, or optical storage. The memory medium may include other types of memory as well, or combinations thereof. In addition, the memory medium may be located in a first computer in which the programs are executed, or may be located in a second different computer that connects to the first computer over a network. In the latter instance, the second computer provides the program instructions to the first computer for execution. Also, the computer system may take various forms, including a personal computer system, mainframe computer system, workstation, network appliance, Internet appliance, personal digital assistant (PDA), television system or other device. In general, the term "computer system" may be broadly defined to encompass any device having a processor which executes instructions from a memory medium.

The memory medium preferably stores a software program for the operation of a measurement device and/or a process module. The software program may be implemented in any of various ways, including procedure-based techniques, component-based techniques, and/or object-oriented techniques, among others. For example, the software program may be implemented using ActiveX controls, C++ objects, JavaBeans, Microsoft Foundation Classes (MFC), or other technologies or methodologies, as desired. A CPU, such as the host CPU, executing code and data from the memory medium includes a means for creating and executing the software program according to the methods described above.

Various embodiments further include receiving or storing instructions and/or data implemented in accordance with the foregoing description upon a carrier medium. Suitable carrier media include memory media or storage media such as magnetic or optical media, e.g., disk or CD-ROM, as well as signals such as electrical, electromagnetic, or digital signals, conveyed via a communication medium such as networks and/or a wireless link.

The software for a measurement device may then be used to monitor and predict the processing conditions of subsequent lithography processes. Preferably, the predefined algorithm for a process step of the lithography process may be incorporated into the software package that interfaces with the measurement device. In this manner, the software may be configured to receive data that may be measured by the measurement device. The software may also be configured to perform appropriate calculations to convert the data into properties of the resist. Additionally, the software may also be configured to compare a property of a resist formed on a product wafer to a property of a resist formed on a reference wafer for a lithography process. In this manner, the software may be configured to convert variations in the properties to variations that may occur in the process conditions. Furthermore, by incorporation of the appropriate algorithm, the software may also be configured to convert the properties of a resist into meaningful data about the process conditions of the lithography process including a characteristic of an exposure step or a characteristic of a post exposure bake step.

A method to evaluate and control a lithography process using field level analysis as described above may provide dramatic improvements over current process control methods. Measuring within wafer variability of critical metrics, or critical dimensions, may provide tighter control of the critical dimension distribution. In addition to improving the manufacturing yield, therefore, the method described above may also enable a manufacturing process to locate the distribution performance of manufactured devices closer to a higher performance level. As such, the high margin product yield may also be improved by using such a method to evaluate and control a lithography process. Furthermore, additional variations in the lithography process may also be minimized For example, a process may use two different post exposure bake units to process one lot of wafers. Two bake units may be used to perform the same process such that two wafers may be processed simultaneously in order to reduce the overall processing time. Therefore, the above method may be used to evaluate and control each bake unit separately. As such, the overall process spread may also be reduced.

The data gathered in accordance with the present invention may be analyzed, organized and displayed in any suitable means. For example, the data could be grouped across the wafer as a continuous function of radius, binned by radial range, binned by stepper field, by x-y position (or range of x-y positions, such as on a grid), by nearest die, and/or other suitable methods. The variation in data may be reported by standard deviation from a mean value, the range of values, and/or any other suitable statistical method.

The extent of the within wafer variation (such as the range, standard deviation, and the like) may be analyzed as a function of wafer, lot, and/or process conditions. For example, the within wafer standard deviation of the measured CD may be analyzed for variation from lot to lot, wafer to wafer, and the like. It may also be grouped, reported, and/or analyzed as a function of variation in one or more process conditions, such as develop time, photolithographic exposure conditions, resist thickness, post-exposure bake time and/or temperature, pre-exposure bake time and/or temperature, and the like. It may also or instead be grouped, reported, and/or analyzed as a function of within wafer variation in one or more of such processing conditions.

The data gathered in accordance the present invention may be used not just to better control process conditions, but also where desirable to better control in situ endpointing and/or process control techniques. For example, data gathered in accordance the present invention may be used in conjunction with an apparatus such as that set forth in U.S. Pat. No. 5,689,614 to Gronet et al. and/or Published European patent Application No. EP 1066925 to Zuniga et al., which are hereby incorporated by reference as if fully set forth herein, to improve the control over localized heating of the substrate or closed loop control algorithms. Within wafer variation data could be fed forward or back to such a tool to optimize the algorithms used in control of local wafer heating or polishing, or even to optimize the tool design. In another example of such localized process control, within wafer variation data could be used to control or optimize a process or tool such as that set forth in one or more of Published PCT Patent Application Nos. WO 99/41434 to Wang or WO 99/25004 to Sasson et al. and/or Published European Patent Application No. 1065567 to Su, which are hereby incorporated by reference as if fully set forth herein. Again, within wafer variation data taken, for example from stand alone and/or integrated measurement tools, could be used to better control and/or optimize the algorithms, process parameters and integrated process control apparatuses and methods in such tools or processes. Data regarding metal thickness and its within wafer variation could be derived from an x-ray reflectance tool such as that disclosed in U.S. Pat. No. 5,619,548 to Koppel and/or Published PCT Application No. WO 01/09566 to Rosenewaig et al., which are hereby incorporated by reference as if fully set forth herein, by eddy current measurements, by ebeam induced x-ray analysis, or by any other suitable method.

Further modifications and alternative embodiments of various aspects of the invention may be apparent to those skilled in the art in view of this description. For example, methods and systems for lithography process control are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims,

What is claimed is:

1. A wafer measurement system for use within a wafer process tool, comprising:

a wafer handler associated with the wafer process tool for feeding wafers between a cassette and any one or more of a plurality of stations of the wafer process tool;

a wafer measurement station forming one of the stations of the wafer process tool, the measurement station having a wafer support in communication with the wafer handler, the measurement station also having therein an optical measurement system forming a scatterometry instrument, the optical measurement system operable to direct a light beam as a spot onto patterned features of a wafer on the wafer support and to obtain characteristic optical signatures for the patterned features; and a data processor analyzing the characteristic optical signatures to obtain a measure of the patterned features on the wafer so that a process carried out by the wafer process tool can be analyzed, the data processor altering wafer processing parameters of at least one of the plurality of the stations of the wafer process tool based upon the characteristic optical signatures such that a first portion of one of the wafers is processed with a first set of process conditions during a step of the process and such that a second portion of the one of the wafers is processed with a second set of process conditions during the step, wherein the first set is different than the second set.

2. The system of claim 1, wherein the optical measurement system includes an objective lens imaging light from the spot on the wafer.

3. The system of claim 1, wherein the wafer handler feeds the wafers into the wafer measurement station with an unspecified wafer orientation relative to the optical measurement system.

4. The system of claim 1, wherein the measure of the patterned features includes at least one dimension of lateral or vertical geometric structure of the patterned features on the wafer.

5. The system of claim 1, further comprising an stage driving the optical measurement system, the wafer support holding the wafer stationary within the wafer measurement station.

6. The system of claim 1, wherein the wafer support is capable of moving a wafer in at least one dimension.

7. The system of claim 1, wherein the wafer support comprises a vacuum chuck.

8. The system of claim 4, wherein the measure of the patterned features includes line width and profile of the patterned features on the wafer.

9. The system of claim 6, wherein the wafer support is rotatable to any of a plurality of angular orientations (q) of the patterned features relative to the optical measurement system without (x,y) translation of the wafer, and a linear stage drives the optical measurement system relative to a radial position (r) of the wafer.

10. The system of claim 6, wherein the wafer support is tiltable to any of a plurality of incidence angles of said light beam onto said wafer.

11. A scatterometry instrument integrated within a wafer measurement station that forms one station of a wafer process tool, the process tool having a wafer handler associated therewith feeding wafers between a cassette and one or more of a plurality of stations of the process tool, wherein the scatterometry instrument comprises:
an optical measurement system for directing a light beam as a spot onto patterned features of a wafer and for obtaining characteristic optical signatures for the patterned features; and
a data processor operable for receiving and analyzing the characteristic optical signatures and obtaining a measure of the patterned features on the wafer such that a process carried out by the wafer process tool can be analyzed, the data processor being further operable to alter process parameters of at least one of the plurality of stations of the process tool based upon the characteristic optical signatures such that a first portion of one of the wafers is processed with a first set of process conditions during a step of the process and such that a second portion of the one of the wafers is processed with a second set of process conditions during the step, wherein the first set is different than the second set.

12. The instrument of claim 11, wherein the measurement system includes an objective lens positioned to image light scattered from the spot on the wafer.

13. The instrument of claim 11, wherein the wafer handler of the process tool and a wafer support in the wafer measurement station provide an unspecified wafer orientation relative to the optical measurement system.

14. The instrument of claim 11, wherein the measure of the patterned features includes at least one dimension of lateral or vertical geometric structure of the patterned features on the wafer.

15. The instrument of claim 14, wherein the measure of the patterned features includes line width and profile of the patterned features on the wafer.

16. A wafer measurement method for cooperative use with a wafer process tool having a wafer handler associated with a cassette of wafers, comprising:
within the wafer process tool after completion of any of one or more process steps carried out in processing stations of the process tool, receiving in an integrated measuring station of the process tool a wafer from a wafer handler associated within the process tool;
measuring an optical characteristic of the wafer using a scatterometry instrument in the integrated measuring station;
analyzing the optical characteristic to obtain a measure of patterned features on the wafer; and
altering one or more process parameters of at least one of the processing stations based on the measure of the patterned features such that a first portion of one of the wafers is processed with a first set of process conditions during a step of a process performed by the wafer process tool and such that a second portion of the one of the wafers is processed with a second set of process conditions during the step, wherein the first set is different than the second set.

17. A method, comprising:
measuring at least one property of patterned features on a wafer at more than one position on the wafer with a measurement device disposed within a lithography cluster tool after at least one step of a lithography process has been performed on the wafer by the tool, wherein the measurement device is configured to use an optical technique to measure the at least one property, and wherein the optical technique comprises scatterometry; and
altering at least one parameter of the lithography cluster tool in response to the at least one properly such that a first portion of the wafer or a different wafer is processed with a first set of process conditions during the lithography process and such that a second portion of the wafer or the different wafer, respectively, is processed with a second set of process conditions during the lithography process, wherein the first set is different than the second set.

18. A method of measuring a wafer within a wafer process tool, comprising:
transferring a wafer to a measurement station of the process tool after a step of a process has been performed on the wafer by the wafer process tool;
measuring an optical characteristic of the wafer at different measurement locations using a measurement instrument within the measurement station, wherein the measurement instrument comprises a scatterometry instrument; and
altering at least one parameter of a process station of the wafer process tool in response to the optical characteristic such that a first portion of the wafer or a different wafer is processed with a first set of process conditions during a step of the process performed by the process station and such that a second portion of the wafer or the different wafer, respectively, is processed with a second set of process conditions during the step performed by the process station, wherein the first set is different than the second set.

19. A method, comprising:
moving a wafer from a process module of a lithography cluster tool to a measurement device disposed within the tool with a robotic wafer handler;

measuring at least one property of the wafer at more than one position on the wafer with the measurement device; and altering at least one parameter of the lithography cluster tool in response to the at least one property such that a first portion of the wafer or a different wafer is processed with a first set of process conditions during a step of a process performed by the lithography cluster tool and such that a second portion of the wafer or the different wafer, respectively, is processed with a second set of process conditions during the step, wherein the first set is different than the second set.

* * * * *